United States Patent [19]
Clarke

[11] 3,957,373
[45] May 18, 1976

[54] QUANTITATIVE DETERMINATION OF ELEMENTS IN ALLOYS

[75] Inventor: Kelvin Arthur Clarke, Beresfield, Australia

[73] Assignee: Commonwealth Steel Company Limited, Australia

[22] Filed: June 20, 1974

[21] Appl. No.: 481,177

Related U.S. Application Data

[63] Continuation-in-part of Ser. No. 104,913, Jan. 8, 1971, abandoned.

[30] Foreign Application Priority Data

Aug. 27, 1970 Australia............................. 2342/70

[52] U.S. Cl.................................. 356/77; 356/74; 356/86; 356/82
[51] Int. Cl.² ........................ G01J 3/40; G01J 3/30
[58] Field of Search .................. 356/74, 77, 81, 82, 356/86

[56] References Cited
OTHER PUBLICATIONS

Fundamentals of Analytical Chemistry; Skoog & West; Holt, Rinehart & Winston, 1963, pp. 682–683.

*Primary Examiner*—Vincent P. McGraw
*Attorney, Agent, or Firm*—Hill, Gross, Simpson, Van Santen, Steadman, Chiara & Simpson

[57] ABSTRACT

A method of quantitative spark emission analysis of a select element in an alloy comprising establishing a basic calibration curve which relates a spectrometer count during a given integration time period to an actual content of the select element in a standard sample of the alloy, determining an influencing factor on the spectrometer count of the select element by the presence of an influencing element in the alloy being analyzed, spectroscopically analyzing the alloy for the select element during the given integration time period and deriving an indicated content of the select element from the basic calibration curve, and adjusting the indicated content of the select element in the alloy being analyzed by the influencing factor so as to derive an actual content of the select element in the alloy.

5 Claims, 6 Drawing Figures

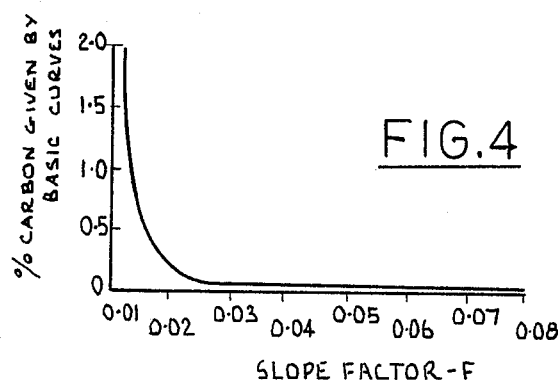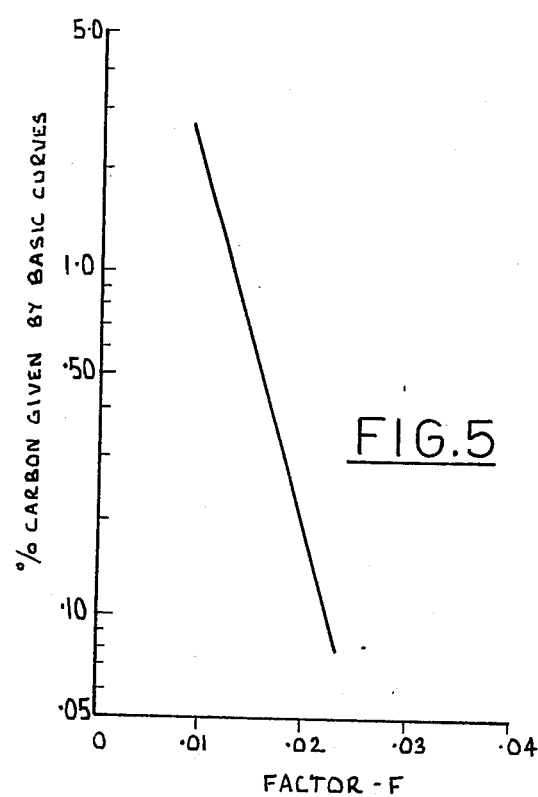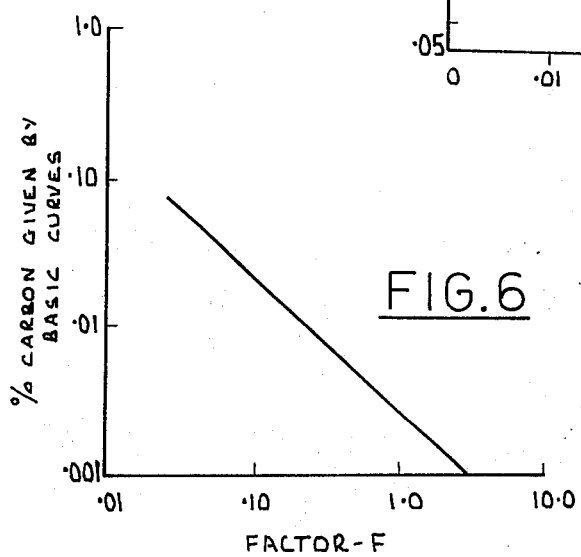

QUANTITATIVE DETERMINATION OF ELEMENTS IN ALLOYS

CROSS-REFERENCE TO RELATED APPLICATION

This is a continuation-in-part of U.S. Ser. No. 104,913, filed Jan. 8, 1971 (now abandoned), which is incorporated herein by reference.

BACKGROUND OF THE INVENTION

1. Field of the Invention

The invention relates to quantitative determination of elements in composite materials and somewhat more particularly to quantitative analysis of elements in alloys, such as carbon in steel, using a direct reading spectrometer and a single calibration curve.

2. Prior Art

Direct reading vacuum emission spectrometers which employ at least one Internal Standard Line are known wherein the line is selected by the spectrometer manufacturers on the basis of particular design considerations and on the premise that the line is influenced in an identical manner to an element line being used for an analysis and that the background count for each analysis line is influenced by the matrix material. In other words, such spectrometers assume that those factors which influence the Internal Standard Line for a particular alloy equally influence all other elements of that alloy to the same extent and that while variations may be observed by changes in the integration time of the spectrometer, and although such times may vary, the analysis of the other elements remains unchanged.

However, the foregoing premise has been proven incorrect and the following demonstration will serve to illustrate the point.

Assuming that a spectrometer was set to integrate for 20 seconds on an original steel sample having a 98% iron matrix, then, for example, a 1% carbon content within this sample may result in a reading of 600 counts. Then, if 5% of the iron within the original steel sample were displaced by an equal amount of nickel so that an alloy or steel was obtained which was comprised of 93% iron, 5% nickel and 1% carbon and this modified alloy was analyzed with the above spectrometer, it would be noed that the count level determining capacitor takes longer to charge to the predetermined value since the Internal Standard Line (i.e., for iron) is of a lower intensity for the modified alloy. In other words, a longer integration time will result and the identical 1% carbon level will give rise to, for example, a reading of 700counts, which is incorrect.

Further, if the nickel within the above modified alloy were displaced by an equal amount of chromium and the further modified sample analyzed with the above spectrometer, prior art would assume that the identical (700) count would be obtained, since the iron content and thus the integration time remained unchanged. However, it has been ascertained that, despite the same integration time, the 1% carbon content in the above chromium-alloy will give rise to a lower reading, for example, 680 counts. This result is attained because the chromium content influences the carbon content readout and not the iron intensity.

In order to attain accurate measurements and in an attempt to overcome the lack of sensitivity in present spectrometers, as demonstrated by the foregoing, analysts have produced numerous calibration curves for various (standard) alloys, for example, a carbon calibration curve is available for 18/8 stainless steel, another curve is available for 24/20 stainless steel, etc. However, quite apart from the vast number of calibration curves required for standard alloys, off-specification alloys which are submitted for analysis cannot be accommodated.

In addition, instrument manufacturers have devised various ways, besides the Internal Standard method, for correcting the errors or inaccuracies resulting from changes in matrix content of alloys. However, these involve tedious mathematical calculations which are based on the matrix material content, for example, on the iron content in a steel, and are only suitable over limited ranges of matrix material content.

SUMMARY OF THE INVENTION

The invention provides a method of quantitative spectroscopic analysis of an element in an alloy with a single calibration curve which substantially eliminates the aforesaid prior art problems.

In the practice of the principles of the invention, one dispenses with the necessity of referring to an Internal Standard, dispenses with the necessity of correcting for various matrix material content and one is able to employ a single integration time period.

The invention is based on the discovery that during spectrometric analysis of alloys, certain elements have an effect on the instrument indicated level of various other elements which are being quantitatively determined. For example, in analysis of steel alloys, it has been established that the manganese and/or chromium content of the steel sample being analyzed for its carbon content, influence the carbon content readout, which is then adjusted in accordance with the principles of the invention, with the aid of a single basic calibration curve so as to obtain a true carbon content in the sample.

The invention comprises a method of quantitative spark emission analysis of an element within an alloy wherein (a) a basic calibration curve is established relating a spectrometer count during a given integration time period to an actual content of that element in a standard sample of such alloy, (b) an influencing factor for the effect of the presence of an influencing element within the standard sample of such alloy is determined, (c) a spectrometer count for the element being analyzed in the alloy during the given integration time period is established and an indicated content of that element is derived from the basic calibration curve, and (d) the indicated content of the element being analyzed is adjusted by the influencing factor so as to derive an actual content of the element in the alloy.

In a preferred embodiment, the invention provides a method of quantitatively analyzing the carbon content in various grades and types of iron alloys, i.e., steels.

BRIEF DESCRIPTION OF THE DRAWINGS

FIG. 4 is a graphical illustration similar to that of FIG. 3, but relating the chromium influencing factor to the derived carbon content; and FIGS. 5 and 6 are graphical illustrations of the graph shown in FIG. 4, separated into two sections for greater accuracy.

DESCRIPTION OF THE PREFERRED EMBODIMENTS

Figure 1:
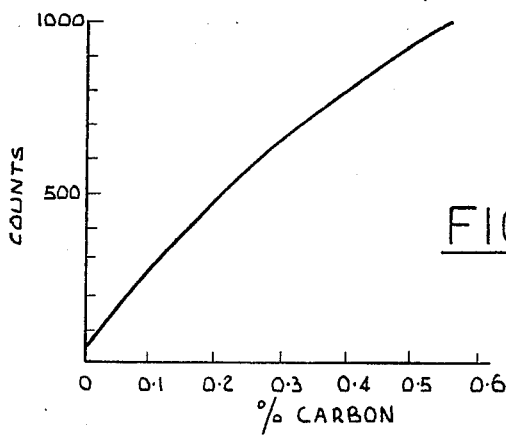
FIG. 1 is a graphical illustration of a typical basic calibration curve for a given range of carbon content in a steel relating spectrometer count to actual amount of carbon in such steel.

The invention provides a method of error-free quantitative spectrometric analysis of an element within an alloy.

The invention is based on the discovery that the presence of certain elements within an alloy cause a false spectrometric reading of the actual content of another element within the alloy. In order to correct such false readings in accordance with the invention, a determination in made as to the influence of various elements within an alloy on the count given by the spectrometer for an element being analyzed and a correction is then made to the instrument indicated element content to compensate for the influence of the "interfering" element within the alloy. For example, in the quantitative spectrometric analysis of carbon in various steel alloys, it has been discovered that manganese and chromium influence the instrument indicated carbon readout. Accordingly, when the invention is utilized for carbon analysis in steel, the derivation of the true carbon content of the alloy is obtained by establishing a basic calibration curve for carbon content, which relates the percentage or amount of carbon present in the alloy to a spectrometric count reading and by establishing a correction curve which relates a correction factor (for a particular element, such as Mn and/or Cr) to the amount of carbon derived from the basic calibration curve. Then, by relating a correction factor derived from the correction curve for a particular instrument measured carbon level or content in the alloy, the actual or true carbon content of the alloy may be determined.

The invention is therefor defined as a method for quantitative analysis of a first element in an alloy containing such element with a direct reading spectrometer wherein (a) a basic calibration curve is first established to relate the spectrometer count to the actual content of the first element in a standard alloy sample; (b) an influencing factor is determined for the effect of the presence of influencing elements within a standard alloy sample; (c) the alloy is spectroscopically analyzed for the first element under instrument conditions substantially identical to those utilized during the establishment of the basic calibration curve and an instrument indicated content of the first element within the alloy is derived from the basic calibration curve; and (d) the aforesaid instrument indicated content of the first element is adjusted by the influencing factor so as to attain the actual content of the first element in the alloy.

Somewhat more particularly, the invention comprises (a) establishing a basic calibration curve which relates a spectrometer count during a given integration time period to an actual content of a first element in a standard sample of an alloy; (b) determining an influencing factor for the effect of the presence of an influencing element in a standard sample of the alloy and relating said influencing factor to the basic calibration curve to derive a slope factor in accordance with the relation.

$$E_1 \cdot I_m \cdot F_s = E_2 \tag{I}$$

wherein $E_1$ is the indicated amount of the first element obtained from the basic calibration curve;

$I_m$ is the amount of said influencing element present in the standard sample of the alloy;

$F_s$ is the slope factor; and $E_2$ is the amount of adjustment necessary to obtain the true amount of said first element in the standard sample of the alloy;

c. spectroscopically analyzing an unknown sample of the alloy having unknown amounts of the first element and the influencing element therein for the influencing element and for the first element during the given integration time period and deriving an indicated content of the first element from the basic calibration curve; and (d) adjusting the indicated count of the first element in the unknown alloy by said influencing factor so as to derive an actual content of the first element in the unknown alloy in accordance with the equation:

$$E_3 = E_1 (1 + I_m F_s) \tag{II}$$

wherein $E_3$ is the true percentage of the first element in an alloy;

$E_1$ is the indicated percentage of the first element in the alloy;

$I_m$ is the amount of the influencing element present in the alloy; and $F_s$ is the slope factor of the influencing element present in the alloy.

In a preferred embodiment, the invention provides a method of quantitatively analyzing the carbon content in various grades and/or types of iron alloys. During the practice of the invention, no reference is required to an Internal Standard and, during carbon analysis, no corrections for variations in the iron content of a steel, either mathematically or by a matrix corrector facility is required. A fixed integration time may be utilized for all steels and the iron spectral line does not have to be monitored.

In order to further facilitate an understanding of the invention by those skilled in the art, a preferred embodiment (i.e., analysis of carbon and steel) will be explained in detail hereinafter so that the details of practicing the invention may be fully appreciated. However, the details are not to be construed as limiting the scope of the invention in any way.

In the analysis of carbon content in steels, it has been established that a given amount of manganese and/or chromium influences the carbon readout for a steel subjected to analysis. The apparent restriction of having to ascertain the level of the influencing elements (i.e., Mn and Cr) before being able to determine the actual carbon content poses no serious problems since in a typical carbon analysis, manganese and chromium are determined simultaneously with the carbon.

A description of a method for deriving basic calibration curves and correction curves for use in spectroscopic analysis of carbon and various steels follows.

BASIC CALIBRATION CURVE

The derivation of the actual or true carbon content of an alloy or steel is obtained by establishing a basic calibration curve for actual carbon content versus spectrometer count and by applying a correction factor to the indicated carbon content derived from the count level or readout. The correction factor is dependent upon the nature of other elements included in the iron-carbon alloy and upon the level of carbon indicated by the spectrometer count to be present in the alloy. Accordingly, to achieve absolute accuracy, a standard sample employed in the establishment of the basic calibration curve should, ideally, consist of iron and carbon only. However, since such ideal samples are not practical (since there is always the possibility that some trace of one or more influencing element may be present in a standard sample), it was determined that the presence of influencing elements below a certain amount provided an accuracy suitable for most practical requirements. In the analysis of carbon in steel, such amounts comprise a maximum of 0.15% for chromium and a maximum of 0.65% for manganese.

Accordingly, standard steel samples having a maximum of about 0.15% chromium and about 0.65% manganese were analyzed by conventional means for carbon content. These standard samples were then sparked on a spectrometer and the counts obtained were plotted against the actually determined carbon content in each sample.

FIG. 1 illustrates a typical basic calibration curve for a carbon content in steel ranging from 0.00 to 0.50%. Similar curves (not shown) were derived in the same manner for carbon content ranges of 0.50 to 1.60% and for ranges of 1.60 to 2.80% so that while reference is made herein to a "single calibration curve," it will be appreciated that more than one such curve may be employed in the analysis of different carbon content ranges.

To study the influence of the manganese content on the indicated carbon content, standard samples were sparked with known carbon and manganese content and with a chromium content below 0.15%. Similarly, to study the influence of the chromium content on the indicated carbon content, standard samples were sparked with known carbon and chromium contents and with a manganese content below about 0.65%. Then, the carbon error, that is the difference between the true carbon content and the carbon content obtained by utilizing the basic calibration curve, was plotted against the manganese and the chromium content, respectively, of the standard samples.

MANGANESE INFLUENCE

Figure 2:
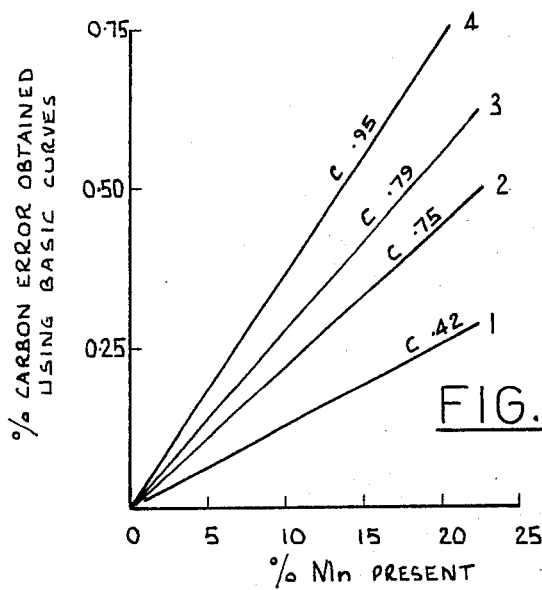
FIG. 2 is a graphical illustration of the correction required on the instrument indicated carbon count in relation to the amount of manganese present in the steel.

The results of the study of the manganese influence on the indicated carbon content are illustrated by the curves in FIG. 2.

Since each line or curve in FIG. 2 represents the correction required due to the amount of manganese present for an indicated carbon content (obtained by utilizing the basic calibration curve), these curves of FIG. 2 may be termed "isocarb" lines. For example, in FIG. 2, if the carbon content indicated by the spectrometer is 0.79%, then line 3 is used to obtain the correction due to manganese.

While there are numerous ways of relating these variables, the most practical way is to arrive at a select factor for each curve or line of FIG. 2. This entails the use of a slope factor, which is constant for each particular curve and then incorporating the carbon content as determined by the basic calibration curve, i.e., the % carbon value of that isocarb. The mathematical equation used is:

$$C_1 \cdot Mn_a \cdot F_s = C_2 \qquad (III)$$

wherein
$C_1$ is the carbon content obtained from the basic calibration curve;
$Mn_a$ is the manganese content present in the alloy being analyzed;
$F_s$ is the slope factor; and
$C_2$ is the percentage carbon adjustment necessary to obtain the correct or true carbon content of the alloy.

Figure 3:
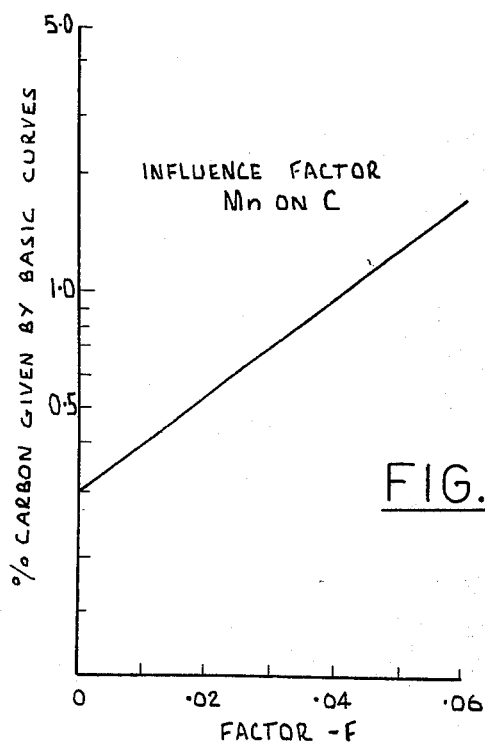
FIG. 3 is a graphical illustration of the relation between the carbon content derived from the basic calibration curve and the manganese influencing factor derived from the graph of FIG. 2.

The slope factor, $F_s$, was then calculated for all of the standard samples studied and the percentage carbon given by the basic calibration curves plotted against the slope factors. FIG. 3 illustrates the graph obtained, with the ordinate being the value of the percentage carbon obtained from the basic calibration curves and the abscissa being the value of the factor $F_s$ to be used in equation (II) above.

As can be seen from FIG. 3, the manganese content of a steel has no influence on the indicated carbon content thereof, if the carbon content is less than 0.30%. This has been verified.

In applying the principles of the invention to obtain the true carbon content of steel, it is necessary to accurately ascertain the manganese (and chromium) content of the steel being analyzed and, having obtained the approximate carbon content in the steel via the basic calibration curve, use the graph of FIG. 3 to obtain a value of $F_s$ and substitute the appropriate values into the mathematical equation set forth below:

$$C_3 = C_1 (1 + Mn_a F_s) \qquad (IIa)$$

wherein
$C_3$ is the true percentage of carbon present in steel;
$C_1$ is the carbon content of the steel as obtained from the basic calibration curve;
$Mn_a$ is the manganese content of the steel; and
$F_s$ is the slope factor.

It will be noted that equation (IIa) is merely a specialized case of equation (I) set forth earlier.

As indicated earlier for practical reasons, the basic calibration curves are based on steel samples having an average manganese content of about 0.65%, and if greater accuracy is desired, the $Mn_a$ value used in equation (Ia) above, should be modified to correspond to (true manganese content −0.65%). The degree of error involved without such a correction is not significant for most analysis, however, with steels having 2% carbon, the correction factor due to manganese influence is extremely large and the foregoing adjustment for actual manganese content should be made with such steels to improve the accuracy of the carbon analysis.

Results obtained using the foregoing procedure are set forth below in Table I, along with comparative results obtained using a gravimetric method (British Standard, BS1121, Pt. II, 1967) for the determination of carbon content in steel.

TABLE I

| Steel Sample No. | % Carbon Before Correction | % Manganese Present | % Carbon After Correction | % Carbon by Gravimetric Method |
|---|---|---|---|---|
| 1 | 0.82 | 13.7 | 1.18 | 1.18 |
| 2 | 0.96 | 15.4 | 1.54 | 1.53 |
| 3 | 0.69 | 9.4 | 0.86 | 0.85 |
| 4 | 0.485 | 4.2 | 0.51 | 0.52 |

CHROMIUM INFLUENCE

The results of the study of the chromium influence on indicated carbon content was completely analogous to that obtained for the manganese content as shown in FIG. 2 and a family of curves similar to those of FIG. 2 were obtained for steels having various chromium content.

Thereafter, the procedure was exactly the same as described above, i.e., slope factors were obtained for each isocarb line and these values were plotted on a graph along the abscissa against corresponding values of carbon along the ordinate. FIG. 4 illustrates the resulting graph.

In order to obtain more accurate slope factors at both the high and the extremely low carbon levels, the graphs of FIG. 4 was replotted in two sections, as shown at FIGS. 5 and 6. Then, by utilizing equation (IIa) above, and substituting the chromium content of the steel for the manganese content, and obtaining the related slope factor values, the true carbon content of any grade of chromium-bearing steel was readily ascertained.

Results obtained using the foregoing procedure are set forth below in Table II, along with comparative results using the aforenoted gravimetric method for determining the carbon content in steel, unless otherwise noted.

TABLE II

| Steel Sample No. | % Chromium Present | % Carbon After Correction | % Carbon by Gravimetric Method |
|---|---|---|---|
| 11 | 12.90 | 0.086 | 0.088 |
| 12 | 18.00 | 0.82 | 0.82 |
| 13 | 20.0 | 0.46 | 0.47 |
| 14 | 18.40 | 0.039 | 0.041* |
| 15 | 18.10 | 0.050 | 0.052 |
| 16 | 17.90 | 0.045 | 0.045 |
| 17 | 18.70 | 0.87 | 0.88 |
| 18 | 18.10 | 0.99 | 0.97 |
| 19 | 13.30 | 0.67 | 0.65 |
| 20 | 26.60 | 0.104 | 0.103 |

*Non-aqueous titration method B.I.S.R.A. Report MG/DA/447/68.

It will be appreciated that the above described analysis procedure may be employed with all types and/or grades of steel or with any types of alloy in which an element line count readout is influenced by the presence of another element.

Results obtained using the procedure of the invention on steels having both manganese and chromium therein as major alloying elements are set forth below in Table III, along with comparative results obtained using the aforenoted gravimetric method.

TABLE III

| Steel Sample No. | % Carbon Before Correction | % Carbon After Correction | % Carbon By Gravimetric Method |
|---|---|---|---|
| 30 | 0.35 | 0.45 | 0.46 |
| 31 | 1.39 | 1.94 | 1.96 |

The data shown in Tables I and III above, includes the instrument indicated carbon content values before correction for the influence of manganese and/or chromium and demonstrates the rather large corrections which may be made without error. The order of magnitude of the corrections involved can be obtained for all carbon levels and varying levels of interference elements by the use of the appropriate figures and equations set forth above.

Table IV below, lists an exemplary group of elements which have been determined to influence the indicated level of an element being quantitatively determined by a spectrometer in various alloys:

TABLE IV

| Alloy | Element Being Determined | Analytical Line Employed A | Influencing Element(s) |
|---|---|---|---|
| Steel or Iron | Manganese | 1921 | Chromium, Molybdenum |
| Steel or Iron | Phosphorus | 1783 | nil |
| Steel or Iron | Nickel | 2316 | iron |
| Steel | Aluminum | 1863 | nil |
| Steel | Iron | 1961 | molybdenum |
| Nickel Based | Manganese | 1921 | chromium, molybdenum |
| Nickel Based | Phosphorus | 1783 | nil |
| Nickel Based | Sulphur | 1807 | Mode of combination of sulphur |
| Nickel Based | Aluminum | 1863 | nil |
| Steel or Iron | Carbon | 1930.9 | manganese, chromium |

With all alloys, a single basic calibration curve is established in accordance with the procedure set forth earlier for carbon, and is used in conjunction with a single correction curve, established in accordance with the procedure set forth earlier for the influence of the manganese and/or chromium content on the instrument indicated carbon readout, to obtain an accurate quantitative determination of an element within an alloy.

In order to further delineate the advantages of the invention over the internal standard method of analyzing, say carbon content in steel, the following outline demonstrations are set forth.

INTERNAL STANDARD METHOD

For purposes of this demonstration, the calibration of one channel, namely, carbon for the range 0.00 to 0.50 %, will be considered.

First, a range of calibration standards must be obtained from a suitable source. The standards, unless certified, must be analyzed for carbon by conventional means and it must be assured that in all of the standard samples, the matrices are similar. For practical purposes, instruments are generally calibrated for a plain carbon steel of at least 98.5% iron. In such instance, the iron is the internal standard. This means that the iron concentration will control the period of time for which the instrument will integrate.

The spectrometer is now set to integrate for 20 seconds on a steel having 99% iron. This means that, as the instrument is sparking, two capacitors are charging via the electronic circuits of the instrument, namely, the capacitor connected to the photomultiplier monitoring the iron line and the capacitor associated with the carbon line. The iron capacitor acts, in effect, as a switching device. That is, when it reaches a set charge, the integration process is stopped. The charge accumulated on the carbon capacitor is then fed to measuring circuits whereby a count is provided.

For demonstration purposes, assume that the standard steels, of which there are six, have a certified carbon content of, for example, 0.05% C, 0.15% C, 0.28% C, 0.36% C, 0.42% C and 0.49% C. These samples are then sparked and because they have a similar iron concentration, for example 99% ± 0.5, a similar integration time period will be attained.

It is to be noted that iron concentration could vary up to 2% to 3% (disregarding interelement effects) with little variation in carbon readout obtained. Thus, the results with the aforesaid standards samples are:

0.05% C — 55 counts
0.15% C — 130 counts
0.28% C — 250 counts
0.36% C — 320 counts
0.42% C — 390 counts
0.49% C — 450 counts The foregoing values are then plotted on a graph showing the relation between actual carbon content versus counts.

The instrument is now calibrated for plain carbon steels and unknown plain carbon steels can now be analyzed. The counts obtained on these unknowns are converted to direct percentages from the soprepared graph.

However, if the foregoing graph were used to determine the carbon content of, for example, a 20% Cr + 10% Ni steel (i.e., 70% Fe) an incorrect result would be obtained, the reason being that (disregarding interelement effects) with the above CrNi steel, the iron capacitor of the instrument will take a longer time period to charge up to the set level than with a steel of, for example, 98% Fe because of the rate of charge of the Internal Standard channel. Accordingly, the carbon value obtained for the CrNi steel will be considerably above the correct or actual value.

To overcome the foregoing problem, a calibration curve must be prepared for each type of steel, based on iron and alloy content. Typically, this involves preparing a vast number of calibration curves to cover the normally produced steel types in a given steelworks. Even then, all samples presented for analysis would not be covered since, typically, many production samples do not conform to the normally recognized steel specifications. This situation frequently occurs, for example, with samples taken during the melting and refining process of steel production, especially when a rapid analysis is required.

CLARKE METHOD

With the invention, a single basic calibration curve is prepared to cover the carbon range of interest. The resulting curve is then useful with all sheets having a carbon content within this range, irrespective to overall composition, provided that the appropriate corrections are applied.

Assume a steel sample having a composition of 0.6% C, 21.95% Cr and 1.55% Mn is being analyzed. An apparent carbon content of 0.45% will be obtained by referring the instrument readout count to the basic calibration curve. Then the correction factors for the influence of Cr and Mn are applied to this apparent carbon content.

Referring to FIGS. 4 or 5, one finds that the influence factor for Cr in a steel containing an indicated or apparent carbon content of 0.45% is 0.016. Substituting these values in an equation analogous to equation (IIa) set forth earlier, one obtains:

$C_3 = C_1 (1 + Cr_a F_s)$
$= .45 (1 + 21.95 \times 0.016)$
$= .45 \times 1.35$
$= .608$ The foregoing carbon value may be regarded as being "true" carbon only with respect to the Cr influence and now becomes the apparent carbon value to be used in calculating the correction due to the Mn influence. Referring to FIG. 3, one obtains an influence factor due to Mn of 0.0235 and by substituting these values into equation (IIa) above, one obtains:

$C_3 = .608 [1 + (1.55 - 0.65) \times 0.0235]$
$= .621$

Thus, the true carbon content of the sample is 0.62%. For the sake of comparison, the above calculation, without an adjustment for true Mn content, results in 0.623.

Of course, during actual working conditions, these calculations need not be carried out each time an analysis is performed. A chart of precalculated corrections for each element involved may be provided and the analyst would merely consult such a chart.

As is apparent from the foregoing specification, the present invention is suceptible of being embodied with various alterations and modifications which may differ particularly from those that have been described in the preceding specification and description. For this reason, it is to be fully understood that all of the foregoing is intended to be merely illustrative and is not to be construed or interpreted as being restrictive or otherwise limiting of the present invention, excepting as it is set forth and defined in the hereto-appendant claims.

I claim as my invention:

1. A method for quantitative spark emission analysis of a first element in an alloy, comprising the steps of:
   a. establishing a basic calibration curve which relates a spectrometer count during a given integration time period to an actual content of said first element in a standard sample of said alloy;
   b. determining an influencing factor for the effect of the presence of an influencing element in a standard sample of said alloy and relating said influencing factor to said basic calibration curve to derive a slope factor in accordance with the relation:

$$E_1 \cdot I_m \cdot F_i = E_2$$

wherein $E_1$ is the indicated amount of said first element obtained from said basic calibration curve;

$I_m$ is the amount of said influencing element present in the standard sample of said alloy;

$F_s$ is the slope factor; and $E_2$ is the amount of adjustment necessary to obtain the true amount of said first element in the standard sample of the alloy;

c. spectroscopically analyzing an alloy having unknown amounts of said first element and said influencing element therein for said influencing element and for said first element during said given integration time period and deriving an indicated content of said first element from said basic calibration curve; and d. adjusting said indicated count of said first element in said alloy by said influencing factor so as to derive an actual content of said first element in said alloy in accordance with the relation:

$$E_3 = E_1 (1 + I_m F_x)$$

wherein $E_3$ is the true percentage of the first element in said alloy;

$E_1$ is the indicated percentage of the first element in said alloy;

$I_m$ is the amount of the influencing element present in said alloy; and $F_s$ is the slope factor of the influencing element present in said alloy.

2. A method as defined in claim 1 wherein the first element is carbon, the alloy is steel and the influencing element is selected from the group consisting of Mn, Cr and mixtures thereof.

3. A method as defined in claim 1 wherein step (a) includes establishing a basic calibration curve for each of a plurality of given content ranges of the first element in the alloy.

4. A method as defined in claim 1 wherein step (b) includes establishing a plurality of influencing factors for each of a plurality of given content ranges of an influencing element in the alloy.

5. A method as defined in claim 4 wherein step (b) further includes a basic correction curve relating the slope factor for each of said plurality of influencing factors to a derived first element content in the alloy based on said basic calibration curve.

* * * * *